United States Patent

Mokhallalati et al.

Patent Number: 5,565,577

Date of Patent: Oct. 15, 1996

[54] PROCESS FOR PREPARING 1-ALKYARYL-2-ALKYL-5-FORMYLIMIDAZOLE

[75] Inventors: Mohamed K. Mokhallalati, King of Prussia; Lendon N. Pridgen, Collegeville; Susan Shilcrat, Bala Cynwyd; Joseph Weinstock, Phoenixville, all of Pa.

[73] Assignee: SmithKline Beecham Corporation, Philadelphia, Pa.

[21] Appl. No.: 403,761

[22] PCT Filed: Sep. 7, 1993

[86] PCT No.: PCT/US93/08390

§ 371 Date: Mar. 22, 1995

§ 102(e) Date: Mar. 22, 1995

[87] PCT Pub. No.: WO94/06776

PCT Pub. Date: Mar. 31, 1994

[30] Foreign Application Priority Data

Sep. 23, 1992 [GB] United Kingdom ............... 9220068

[51] Int. Cl.⁶ .................. C07D 233/64; C07D 233/90
[52] U.S. Cl. ............................................. 548/333.5
[58] Field of Search ............................... 548/333.5

[56] References Cited

U.S. PATENT DOCUMENTS

| | | | |
|---|---|---|---|
| 4,194,049 | 3/1980 | Field et al. ................... | 548/336 |
| 4,340,598 | 7/1982 | Furukawa et al. ............ | 548/333.5 X |
| 4,482,723 | 11/1984 | Reiter ........................... | 548/333.5 |
| 4,602,093 | 7/1986 | Baldwin et al. .............. | 548/333.5 X |
| 5,013,854 | 5/1991 | Bynnell ......................... | 549/496 |
| 5,023,336 | 6/1991 | Shigehara et al. ........... | 548/110 |
| 5,075,452 | 12/1991 | Kirchlechner et al. ...... | 548/333.5 X |
| 5,234,917 | 8/1993 | Finkelstein et al. .......... | 514/397 |

FOREIGN PATENT DOCUMENTS

| | | | |
|---|---|---|---|
| 0579212 | 1/1994 | European Pat. Off. ...... | 548/333.5 |
| 94-06776 | 3/1994 | WIPO ............................ | 548/333.5 |

OTHER PUBLICATIONS

J. Org. Chem., 52, pp. 2714–2726 1987 Reiter II.
Angew. Chem. Internat. Ed., 14, pp. 86–94 1975 Reichardt et al.

Primary Examiner—Floyd D. Higel
Attorney, Agent, or Firm—Mary E. McCarthy; Stephen Venetianer; Edward T. Lentz

[57] ABSTRACT

This invention relates to a process for preparing 1-alkylaryl-2-alkyl-5-formylimidazoles of the formula (I):

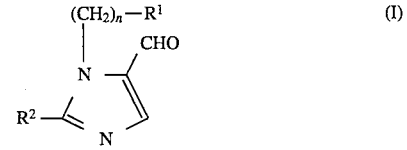

which are useful intermediates in the preparation of 1,2,5-substituted imidazoles having angiotensin II receptor antagonist activity.

11 Claims, No Drawings

PROCESS FOR PREPARING 1-ALKYARYL-2-ALKYL-5-FORMYLIMIDAZOLE

This application is a of U.S. Pat. No. 931/08390 filed Sep. 7, 1993.

The present invention relates to a process for preparing useful intermediates in the synthesis of substituted imidazole compounds. Such compounds are described in EP Application No. 90 306 204.0 as being angiotensin II receptor antagonists useful in the treatment of hypertension, congestive heart failure, renal failure, and glaucoma.

BACKGROUND OF THE INVENTION

EP Application No. 90 306 204.0 describes a process for the preparation of imidazole intermediates which comprises a high pressure liquid ammonia condensation of an alkyl alkylimidate with dihydroxyacetone to give 2-alkyl-5hydroxymethylimidazoles. Subsequent N-alkylarylation and oxidation yields 1-alkylaryl-2-alkyl-5-formylimidazoles. Although this process produces the key imidazole intermediates necessary for preparing the angiotensin II receptor antagonizing imidazoles described therein, the high pressure step limits the quantity of compound that can be produced using this method. Therefore, there is a need for an alternate method for the preparation of the imidazole intermediates on a commercial scale.

A further challenge in developing an alternate process is the fact that the regiospecific synthesis of N-substituted imidazoles is not a straight forward operation. Few syntheses exist which result in the exclusive formation of 1,2,5-substitution on the imidazole ring.

It has now been found that the substituted 5-formylimidazole intermediates can be prepared by reacting a 2-halo-2-propenal-3-alkyl ether,-3-alkyl thioether, or -3-amine with a N-( 1-iminoalkyl)aminoalkylaryl compound to produce said intermediates efficiently in high yield and high purity. The efficiency of the process and the quality and yields of the imidazole intermediates are particularly important when preparing compounds on a large scale for therapeutic use.

DESCRIPTION OF THE INVENTION

The present invention provides a process for the preparation of a compound of formula (I):

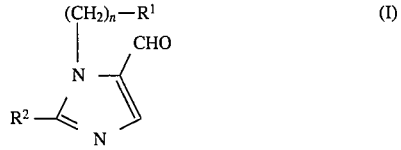

wherein:

$R^1$ is hydrogen, phenyl, biphenyl, or naphthyl, with each group being unsubstituted or substituted by one to three substituents selected from Cl, Br, F, I, $C_1$–$C_6$alkyl, nitro, A-$CO_2R^6$, tetrazol-5-yl, $C_1$–$C_6$alkyl, $SO_2NHR^6$, $NHSO_2R^6$, $SO_3H$, $CONR^6R^6$, CN, $SO_2C_1$–$C_6$alkoxy, hydroxy, $SC_1$–$C_6$alkyl, $NHSO_2R^6$, $PO(OR^6)_2$, $NR^6R^6$, $NR^6COH$, $NR^6COC_1$–$C_6$alkyl, $NR^6CON(R^6)_2$, $NR^6COW$, W, $SO_2W$;

$R^2$ is hydrogen, $C_2$–$C_{10}$alkyl, $C_3$–$C_{10}$alkenyl, $C_3$–$C_{10}$alkynyl, $C_3$–$C_6$cycloalkyl, or $(CH_2)_{0-8}$phenyl unsubstituted or substituted by one to three substituents selected from $C_1$–$C_6$alkyl, nitro, Cl, Br, F, I, hydroxy, $C_1$–$C_6$alkoxy, $NR^6R^6$, $CO_2R^6$, CN, $CONR^6R_6$, W, tetrazol-5-yl, $NR^6COC_1$–$C_6$allyl, $NR^6COW$, $SC_1$–$C_6$alkyl, $SO_2W$, or $SO_2C_1$–$C_6$alkyl;

W is $C_qF_{2q+1}$, wherein q is 1–3;

A is —$(CH_2)_n$—,—CH=CH—,—$O(CR^4R^5)_m$—, or—$S(CR^4R^5)_m$—;

each $R^4$, $R^5$ independently is hydrogen, $C_1$–$C_6$alkyl (unsubstituted or substituted by phenyl, biphenyl, naphthyl or $C_3$–$C_6$cycloalkyl), phenyl, biphenyl, or naphthyl (each of which is unsubstituted or substituted by one to three substituents selected from Cl, Br, I, F, $C_1$–$C_6$alkyl, $(C_1$–$C_5$alkenyl)$CH_2$,$(C_1$–$C_5$alkynyl)$CH_2$, $c_1$–$C_6$alkoxy, $C_1$–$C_6$alkylthio, $NO_2$, $CF_3$, $CO_2R^6$, or OH), $C_3$–$C_6$cycloalkyl, or phenyl($C_1$–$C_2$alkyl) unsubstituted or substituted by phenyl;

each $R^6$ independently is hydrogen, $C_1$–$C_6$alkyl, or $(CH_2)_n$phenyl;

each n independently is 0–4; and each m independently is 1–4; or a pharmaceutically acceptable salt thereof, which comprises reacting a compound of formula (II):

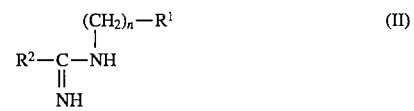

wherein:

$R^1$, $R^2$ and n are as defined above for formula (I), with a compound of formula (III):

wherein:

X is Cl, Br, F, or I; and

Y is —$OR^3$, —$SR^3$, or-$N(R^3)_2$, wherein $R^3$ is $C_1$–$C_6$alkyl, under basic conditions and in solvent and, thereafter, optionally forming a pharmaceutically acceptable salt.

Preferably, the process can be used to prepare compounds of formula (I) in which:

$R_1$ is phenyl, biphenyl, or naphthyl, with each group being unsubstituted or substituted by one to three substituents selected from Cl, Br, F, $CF_3$, C 1-C6alkyl, nitro, $CO_2R^6$, $OCR^4R^5CO_2R^6$, tetrazol-5-yl, $C_1$–$C_6$alkoxy, hydroxy, CN, or $SO_2NHR^6$;

n is 1 or 2; and $R^2$ is $C_2$–$C_8$alkyl.

It should be noted that, as used herein, the terms alkyl, alkenyl, alkoxy and alkynyl mean carbon chains which are branched or unbranched with the length of the chain determined by the descriptor preceding the term. Also, the term alkylaryl means —$(CH_2)_nR^1$ wherein $R^1$ and n are as defined for formula (I) compounds.

In particular, the process can be used to prepare compounds of formula (I) in which $R^1$ is phenyl or naphthyl substituted by $CO_2R^6$, preferably $CO_2H$, n is 1, and $R^2$ is $C_2$–$C_8$alkyl, preferably n-butyl. Most particularly, the process can be used to prepare 4-[(2-n-butyl-5-formyl- 1H-imidazol- 1-yl)methyl]benzoic acid and 4-[(2-n-butyl-5-formyl-1H-imidazol-1-yl-methyl]naphthoic acid.

Suitably, the reaction is carried out on compounds of formula (II) in which $R^1$, $R^2$, and n are as required in the desired formula (I) product. Preferably, the process is conducted with formula (II) compounds in which $R^1$ is phenyl or naphthyl substituted by $CO_2R^6$, preferably $CO_2H$, n is 1, and $R^2$ is $C_2$–$C_8$alkyl, preferably n-butyl.

Suitably, the reaction is carried out on compounds of formula (III) in which X is Cl, Br, F, or I, preferably Br, and Y is —O—$C_1$–$C_6$alkyl, preferably iso-propyloxy.

Preferably, the reaction is carried out by reacting a 2-halo-2-propenal-3-alkyl ether, such as 2-bromo-3-(1-methylethoxy)-2-propenal, with a N-(1-iminoalkyl)aminoalkylaryl compound, such as N-(1-iminopentyl)-4-(aminomethyl)benzoic acid or N-(1-iminopentyl)-4-(aminomethyl)naphthoic acid, in the presence of base, such as an inorganic base, for example, sodium or potassium carbonate, or sodium or potassium hydroxide, preferably potassium carbonate, in solvent, such as water/organic solvent mixture, for example, water and tetrahydrofuran, water and acetonitrile, or water and chloroform containing 1, 4, 7, 10, 13, 16-hexaoxacyclooctadecane (18-Crown-6), preferably water and tetrahydrofuran. Suitably, the reaction is carried out at a temperature of between about 10° C. and about 80° C., preferably between about 25° C. and about 65° C.

Alternately, the reaction is carried out in the presence of an organic base and in an organic solvent. For example, a 2-halo-2-propenal-3-alkyl ether, such as 2-bromo-3-(1-methylethoxy)-2-propenal, is reacted with a N-(1-iminoalkyl)aminoalkylaryl compound, such as ethyl N-(1-iminopentyl)-4-(aminomethyl)benzoate or ethyl N-(1-iminopentyl-4-(aminomethyl)naphthoate, in the presence of an organic base, for example, triethylamine, diisopropylethylamine, or dimethylaminopyridine, preferably triethylamine, in an organic solvent, such as chlorinated hydrocarbons, for example, chloroform dichloromethane, or 1,2-dichloroethane, preferably chloroform. Suitably, the reaction is carried out at a temperature of between about 10° C. and about 80° C., preferably between about 25° C. and about 65° C.

Alternately, the reaction is carried out using the N-(1-iminoalkyl)-aminoalkylaryl compounds of formula (II) as the base. For example, a 2-halo-2-propenal-3-alkyl ether, such as 2-bromo-3-(1-methylethoxy)-2-propenal, is reacted with a N-(1-iminoalkyl)aminoalkylaryl compound, such as ethyl N-(1-iminopentyl)-4-(aminomethyl)benzoate or ethyl N-(1-iminopentyl)-4-(aminomethyl)naphthoate, in the presence of a catalytic amount of acetic acid, in an organic solvent, such as chlorinated hydrocarbons, for example, chloroform, dichloromethane, or 1,2-dichloroethane, preferably chloroform. Suitably, the reaction is carried out at a temperature of between about 10° C. to about 80° C., preferably between about 25° C. and about 65° C.

The starting N-(1-iminoalkyl)aminoalkylaryl compounds of formula (II) are prepared by reacting an alkyl alkylimidate, $R^2C(=NH)$—O—$C_1$–$C_6$alkyl, for example, methyl valerimidate, with an aminoalkylaryl compound, such as 4-(aminomethyl)benzoic acid.

The starting 2-halo-2-propenal alkyl ether compounds of formula (III) are prepared by halogenation and deprotection of malonaldehyde bisdialkyl acetal, followed by O-alkylation of the 2-halo-malonaldehyde intermediate.

The invention is illustrated by the following example. The example is not intended to limit the scope of this invention as defined hereinabove and as claimed hereinbelow.

EXAMPLE 1

Preparation of
4-[(2-n-Butyl-5-formyl-1H-imidazol-1-yl)methylbenzoic Acid i. Preparation of Methyl Valerimidate Hydrochloride A 10 gallon, glass-lined fixed reactor was charged with 7.0 kg (84.6 mol) of valeronitrile and 2.96 kg (92.2 mol, 1.1 eq) of methanol. The solution was stirred with cooling to about 5° C. under an atmosphere of nitrogen. A flow of hydrogen chloride gas from a gas cylinder was bubbled into the solution below the surface of the mixture at a rate such that the reaction temperature did not exceed 15° C. After about one hour, 3.67 kg (101 tool, 1.19 eq) of hydrogen chloride had been disbursed from the gas cylinder and addition was stopped. Stirring was continued for an additional 18 h at 0° C. Tert-butyl methyl ether (9.7 kg) was added to the suspension and stirring was continued for 3 h at 0° C. The slurry was then centrifuged under an atmosphere of nitrogen. After drying overnight under nitrogen and for several hours under reduced pressure at ambient temperature the product weighed 9.66 kg (76% yield uncorrected for purity) and had amp of 91°–92° C. The crude product was hygroscopic and was stored in sealed bottles under nitrogen at −5° C.

ii. Preparation of N-(1-iminopentyl)-4-(aminomethyl)benzoic acid

A 22 L, three-necked round bottom flask equipped with an air-powered mechanical stirrer was placed under a nitrogen atmosphere. The vessel was charged with methyl valerimidate hydrochloride (2.5 kg, 16 mol) and dimethylformamide (9.2 L). A thermometer was attached and the suspension cooled to 0°–15° C. with a cooling bath. Triethylamine (2.3 L) was added to the reaction at such a rate so that the internal temperature did not exceed 25° C. The cooling was stopped and the reaction was allowed to stir 1 hour. The reaction mixture was vacuum filtered using a Büchner funnel and a carboy (20 L). The filter cake was washed with additional dimethylformamide (1.0 L) and force-air dried for 15 min. The combined filtrates were saved. Another clean 22 L, three-necked round bottom flask equipped as above was placed under nitrogen. The vessel was charged with the combined filtrates from above followed by triethylamine (1.6 L) and 4-(aminomethyl)benzoic acid (1.7 kg, 11.5 mol). The thermometer was attached and the suspension was heated to an internal temperature of 65° C. with a heating mantle and a temperature controller. The heating was continued for 20 hours. The reaction was cooled to ambient temperature and filtered to yield 2.5 kg of product; 92% uncorrected yield.

iii. Preparation of 2-bromo9-malonaldehyde

A 12 L, three-necked round bottom flask was equipped with an air-powered mechanical stirrer with shaft, paddle, adapter, and thermometer was charged with 2.75 L of water and 110 mL of 12 N hydrochloric acid (1.32 mol). The addition funnel was charged with 2.5 kg of malonaldehyde bis(dimethyl acetal (15.24 mol) which was then added to the stirred aqueous mixture in one portion. Stirring was continued for 30 rain and a clear solution resulted. The reaction mixture was then cooled to 5° C. using an ice-water bath. A 1 L addition funnel was charged with 790 mL of bromine (15.34 mol) and added to the reaction mixture at a rate such that the temperature did not exceed 25° C. (approximately 30 min). The cooling bath was removed and the reaction mixture was allowed to stir at ambient temperature 1 hour. The reaction mixture is colorless to slightly yellow at this point. The solution was transferred to a 10 L round bottom flask and concentrated on the rotary evaporator at aspirator pressure (water bath 40° C.) to approximately one-half the original volume. The reaction suspension was removed from the rotary evaporator and cooled at 10° C. for 18 hour. Using a benchtop Büchner funnel and carboy (20 L), the resultant slurry was vacuum filtered. The solid was washed with 50% aqueous methanol (0.50 L) and force-air dried 2 hours. The mother liquor was returned to the 10 L round bottom flask and concentrated to approximately one-half its original volume. The flask was removed from the rotary evaporator and cooled (10° C.) for 18 hours where additional solid emerged (331 g). The combined dried product was transferred to glass jars for storage to avoid contact with metal and was stored under refrigeration. This material was used as obtained; (2.0 kg, 86% uncorrected yield).

iv. Preparation of 2-bromo-3-(1-methylethoxy)-2-propenal

With moderate agitation, a 20 gallon reactor system was charged with cyclohexane (29.12 L), 2-bromo-malonaldehyde (2.33 kg), p-toluenesulfonic acid monohydrate 43.94 g, and 2-propanol (4.65 L). The contents of the reactor were heated to allow for the removal of distillate under atmospheric pressure (jacket temp. 95° C. and process temp. at 66.4° C.). A total of 16 L of distillate was removed from the reaction via the cooling tower. This represents approximately 47% of the total volume of cyclohexane/2-propanol (33.77 L) being removed from the reactor. The reaction solution was cooled to near ambient temperature and transferred to a 10 gallon reactor system at 40° C. An additional 6 L of distillate was removed under vacuum (~64 torr, jacket temp. 62° C., and reaction temp. 25° C.). The mobile dark orange oil was drained from the vessel and transferred to a rotary evaporator receiver flask and further concentrated under house vacuum at ~30° C. using a rotary evaporator. About 0.2 L more of solvent was removed. Total product obtained was 3.072 kg (16 mol, 103% yield). The product was used as obtained in the next step. This material is unstable and must be kept in a freezer (<−5° C., under nitrogen). The shelve-life is about 2 weeks.

v. Preparation of 4-[(2.butyl-5-formyl-1H-imidazol-1-yl)methyl]benzoic acid

A 10 gallon, glass-lined fixed reactor was charged sequentially under nitrogen gas with tetrahydrofuran (17.96 L), N-(1-iminopentyl)-4-(aminomethyl)benzoic acid (2.2 kg, 9.4 mol), potassium carbonate (1.94 kg), and water (2.19 L). The suspension was then stirred. 2-bromo-3-(1-methylethoxy)-2propenal (1.99 kg, 10.3 mol) was added in one portion using ~0.3 L tetrahydrofuran as rinse. The stirred mixture was heated to reflux (63° C.). Reflux was continued for 3 hours additional amounts of 2-bromo-3-(1-methylethoxy)-2-propenal (0.36 kg, 0.2 mol) was added to the vessel using 0.1 L tetrahydrofuran as rinse. After 4.0 hours reflux, additional 2-bromo-3-( 1-methylethoxy)-2-propenal (0.18 kg, 0.1 mol) was added to the vessel using 0.1 L tetrahydrofuran as rinse. After 7.0 hours total reflux time, the reaction was cooled to 25° C. and allowed to stand overnight with stirring. Water (3.6 L) was added to the vessel to dissolve any solids present and the solution was stirred 15 min. The solution was transferred to a 20 gallon, glass-lined fixed reactor. The original reactor was rinsed with 0.36 L of water which was also added to the 20 gallon vessel. This vessel was charged with ethyl acetate (21.5 L) and the suspension was stirred for 5 rain and then allowed to settle. The dark aqueous alkaline product layer was transferred to a carboy (20 L) then added to a gallon vessel. The 20 gallon vessel was charged with water (2.9 L) and the suspension was stirred 5 rain then allowed to settle. The bottom aqueous layer was collected and added to the 10 gallon vessel while the top ethyl acetate layer was collected for disposal. The basic (pH 10.05) aqueous solution was acidified with 6 N hydrochloric acid (2.51 L) to pH 5.2 then was transferred to a 20 gallon vessel. The 10 gallon vessel was rinsed with methylene chloride (26 L) and added to the 20 gallon vessel. The contents of the vessel were stirred for 10 min and the layers allowed to separate. The lower organic layer was transferred to a carboy (20 L). The 20 gallon vessel was charged with 4.3 L of methylene chloride and stirred for 5 min and then allowed to settle. After the phases separated, the bottom phase was collected in a carboy. The procedure was repeated once more with 4.3 L of methylene chloride. The combined methylene chloride extracts were added to a 10 gallon vessel and water was added (2.9 L). The suspension was stirred for 5 min then allowed to settle. The bottom organic layer was collected and placed in a portable 50 L glass tank. Under fast agitation, 0.67 kg of magnesium sulfate and 0.13 kg of activated charcoal were added and the suspension was filtered through a Büchner funnel containing Celite® under vacuum. The 10 gallon vessel was charged with the methylene chloride solution and the solvent was removed under vacuum until about 5 L remained. The reactor was then charged with 2-butanone (5.17 L) and solvent was removed under vacuum until the volume was 4-5 L. Ethyl acetate was added (13 L) and the suspension was stirred 16 hours. At this time, the solid was removed by filtration using a Büchner funnel under vacuum. The collected solid was rinsed with a mix of 2-butanone:ethyl acetate (10:90) and dried overnight under vacuum. The yield obtained was 1457 g (5.08 mol, 94.0% purity).

It is to be understood that the invention is not limited to the embodiment illustrated hereinabove and the right to the illustrated embodiment and all modifications coming within the scope of the following claims is reserved.

What is claimed is:

1. A process for the preparation of a compound of formula (I):

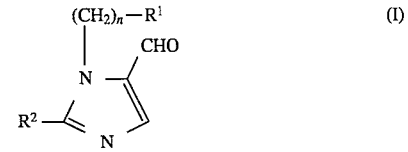

wherein:

$R_1$ is hydrogen, phenyl, biphenyl, or naphthyl, with each group being unsubstituted or substituted by one to three substituents selected from Cl, Br, F, I, $C_1$–$C_6$alkyl, nitro, A-$CO_2R^6$, tetrazol-5-yl, $C_1$–$C_6$alkyl, $SO_2NHR^6$, $NHSO_2R^6$, $SO_3H$, $CONR^6R^6$, CN, $SO_2C_1$–$C_6$alkoxy, hydroxy, $SC_1$–$C_6$alkyl, $NHSO_2R^6$, $PO(OR^6)_2$, $NR^6R^6$, $NR^6COH$, $NR^6COC_1$–$C^6$alkyl, $NR^6CON(R^6)_2$, $NR^6COW$, W, $SO_2W$;

$R^2$ is hydrogen, $C_2$–$C_{10}$alky, $C_3$–$C_{10}$alkenyl, $C_3$–$C_{10}$alkynyl, $C_3$–$C_6$cycloalkyl, or $(CH_2)_{0-8}$phenyl unsubstituted or substituted by one to three substituents selected from $C_1$–$C_6$alkyl, nitro, Cl, Br, F, I, hydroxy, $C_1$–$C_6$alkoxy, $NR^6R^6$, $CO_2R^6$, CN, $CONR^6R^6$, W, tetrazol-5-yl, $NR^6COC_1$–$C_6$alkyl, $NR^6COW$, $SC_1$–$C_6$alkyl, $SO_2W$, or $SO_2C_1$–$C_6$alkyl;

W is $C_qF_{2q+1}$, wherein q is 1–3;

A is —$(CH_2)_n$—,—CH=CH—,—$O(CR_4R_5)_m$—, or—$S(CR_4R_5)_m$—;

each $R^4$, $R^5$ independently is hydrogen, $C_1$–$C_6$alkyl (unsubstituted or substituted by phenyl, biphenyl, naphthyl or $C_3$–$C_6$cycloalkyl), phenyl, biphenyl, or naphthyl (each of which is unsubstituted or substituted by one to three substituents selected from Cl, Br, I, F, $C_1$–$C_6$alkyl, ($C_1$–$C_5$alkenyl)$CH_2$,($C_1$–$C_5$alkynyl)$CH_2$, $C_1$–$C_6$alkoxy, $C_1$–$C_6$alkylthio, $NO_2$, $CF_3$, $CO_2R^6$, or OH), $C_3$–$C_6$cycloalkyl, or phenyl($C_1$–$C_2$alkyl) unsubstituted or substituted by phenyl;

each $R^6$ independently is hydrogen, $C_1$–$C_6$alkyl, or $(CH_2)_n$phenyl;

each n independently is 0–4; and each m independently is 1–4; or a pharmaceutically acceptable salt thereof, which comprises reacting a compound of formula (II):

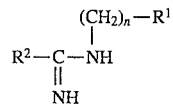

wherein:

$R^1$, $R^2$ and n are as defined above for formula (I), with a compound of formula (III):

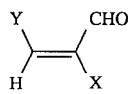

wherein:

X is Cl, Br, F, or I; and

Y is —$OR^3$, —$SR^3$, or—$N(R^3)_2$, wherein $R^3$ is $C_1$–$C_6$alkyl, under basic conditions and in solvent and, thereafter, where necessary forming a pharmaceutically acceptable salt.

2. The process of claim 1 for preparing a compound wherein: $R_1$ is phenyl, biphenyl, or naphthyl, with each group being unsubstituted or substituted by one to three substituents selected from Cl, Br, F, $CF_3$, C 1-C6alkyl, nitro, $CO_2R^6$, —$OCR^4R^5CO_2R^6$, tetrazol-5-yl, $C_1$–$C_6$alkoxy, hydroxy, CN, or $SO_2NHR^6$;

n is 1 or 2; and $R^2$ is $C_2$–$C_8$alkyl.

3. The process of claim 2 for preparing a compound wherein:

$R^1$ is phenyl or naphthyl substituted by $CO_2R^6$;

n is 1; and $R^2$ is $C_2$–$C_8$alkyl.

4. The process of claim 3 for preparing a compound which is 4-[(2-n-butyl-5-formyl- 1H-imidazol- 1-yl)methyl]benzoic acid.

5. The process of claim 4 in which the base is potassium carbonate and the solvent is water and tetrahydrofuran.

6. The process of claim 3 for preparing a compound which is 4-[(2-n-butyl-5-formyl-1H-imidazol-1-yl)methyl]naphthoic acid.

7. The process of claim 6 in which the base is potassium carbonate and the solvent is water and tetrahydrofuran.

8. The process of claim 3 for preparing a compound which is ethyl 4-[(2-n-butyl-5-formyl-1H-imidazol-1-yl)methyl] benzoate.

9. The process of claim 8 in which the base is triethylamine and the solvent in chloroform.

10. The process of claim 3 for preparing a compound which is ethyl 4-[(2-n-butyl-5-formyl-1H-imidazol-1-yl)methyl]naphthoate.

11. The process of claim 10 in which the base is methylamine and the solvent in chloroform.

* * * * *